United States Patent [19]

Walker et al.

[11] 4,358,583

[45] Nov. 9, 1982

[54] EXTRACTION OF POLY(β-HYDROXY BUTYRIC ACID)

[75] Inventors: John Walker, Yarm; Jonathan R. Whitton, Guisborough, both of England

[73] Assignee: Imperial Chemical Industries PLC, London, England

[21] Appl. No.: 287,807

[22] Filed: Jul. 28, 1981

[30] Foreign Application Priority Data

Aug. 13, 1980 [GB] United Kingdom ............... 8026460

[51] Int. Cl.$^3$ ............................................. C08G 63/72
[52] U.S. Cl. ................................. 528/491; 528/361; 528/493; 528/496; 435/135
[58] Field of Search ............... 528/359, 361, 491, 496, 528/493

[56] References Cited

U.S. PATENT DOCUMENTS

| | | | |
|---|---|---|---|
| 3,107,172 | 10/1963 | Baptist | 106/160 |
| 4,101,533 | 7/1978 | Lafferty et al. | 528/491 |
| 4,138,291 | 2/1979 | Lafferty | 435/135 |
| 4,140,741 | 2/1979 | Lafferty et al. | 264/184 |
| 4,324,880 | 4/1982 | Dhein et al. | 528/361 X |

*Primary Examiner*—Earl A. Nielsen
*Attorney, Agent, or Firm*—Cushman, Darby & Cushman

[57] ABSTRACT

Poly (β-hydroxy butyric acid), PHB, is extracted from a suspension of bacterial cells by causing the cells to flocculate, by pH modification, optionally with heating, and then extracting the PHB from the flocculated cells with a suitable extraction solvent. Flocculation of the cells renders subsequent separation of the PHB solution from the cell debris more facile. Preferably lipids are extracted from the flocculated cells before contact with the PHB extraction solvent.

8 Claims, No Drawings

EXTRACTION OF POLY(β-HYDROXY BUTYRIC ACID)

This invention relates to the extraction of poly(β-hydroxy butyric acid) hereinafter referred to as PHB.

PHB is a thermoplastic polyester that is useful as a plastics material. It is accumulated by many bacteria as an energy reserve material in the form of granules within the bacterial cells.

While bacterial cells containing PHB can be used as such as a moulding material, for example as described in U.S. Pat. No. 3,107,172, it is generally described to separate the PHB from the remainder of the bacterial cell material.

Methods that have been proposed to effect this separation include breakage of the cells by methods such as treatment with acetone, followed by extraction of the PHB from the broken cells by treatment with a solvent in which PHB is soluble. Examples of such processes are described in U.S. Pat. Nos. 3,036,959 and 3,044,942 in which the solvents employed are pyridine or mixture of methylene chloride and ethanol. Other extraction solvents for PHB in the form in which it is produced in the bacterial cells include cyclic carbonates such as 1,2-propylene carbonate (see U.S. Pat. No. 4,101,533); chloroform (see U.S. Pat. No. 3,275,610); and 1,2-dichloroethane (see European Patent Application No. 15123).

U.S. Pat. No. 3,275,610 discloses other methods of cell breakage viz. ultrasonic vibration, grinding, French pressing, freezing/thawing cycles and lysozyme treatment, while, as described in the aforementioned European Patent Application, spray or flash drying of the suspension of cells, as produced by culturing the microorganism in an aqueous medium on a suitable carbon and energy source, can also cause sufficient cell breakage to enable the PHB to be extracted from the cells.

One disadvantage of these processes is that it is necessary to separate the PHB-containing solution from the cell debris. Because of the small size of the bacterial cells, and hence of the fragments resulting therefrom, techniques such as filtration have heretofore presented difficulties. This is particularly true where the PHB-containing solution is relatively viscous as in the case where chloroform is utilised as the solvent. As described in the aforesaid European Patent Application, in some cases the PHB can be extracted by a wet process wherein the aqueous bacterial cell suspension, after a suitable cell breakage step, is contacted with a suitable solvent for PHB and then the solvent and aqueous phases are separated. However, separation of the phases may be slow and incomplete.

We have found, that if the bacterial cell suspension is subjected to a flocculation step, sufficient cell breakage may occur during the treatment required to effect flocculation to permit the PHB to be extracted from the cell debris. Also, as a result of the cell flocculation, separation of the PHB-containing solution from the cell debris may be more readily accomplished.

Accordingly we provide a process for the separation of PHB from an aqueous suspension of bacterial cells containing PHB comprising causing said suspension to flocculate by reducing the pH of the suspension to a value within the range 2 to 5 by treatment with an acid, the suspension being treated with an alkali to increase its pH to a value in the range 8 to 12 before acidification and/or heated to a temperature within the range 50° to 200° C. before or after acidification, separating the flocculated cells from the aqueous medium, extracting PHB from the flocculated cells by contacting the latter with a solvent in which the PHB is soluble, and separating the solvent having the PHB dissolved therein from the cell debris.

Examples of such flocculation process are described in UK Patent Specification Nos. 1,062,005 and 1,381,306. Preferably the suspension is flocculated by increasing its pH to a value in the range 8.5 to 12, heating by injecting steam under pressure into the cell suspension, and then acidifying to a pH in the range 3 to 5.

The amount and temperature of the steam is preferably such as to raise the temperature of the cell suspension to a temperature in the range of 60° to 100° C.

The flocculated cells may be separated from the aqueous medium by filtration, sedimentation, flotation, centrifugation or a drying technique such as spray drying.

Before being contacted with the PHB-extraction solvent, the flocculated cells are preferably contacted with a solvent in which the lipids associated with the bacterial cell are soluble but in which PHB is insoluble. Examples of such solvents include methanol and acetone. The extraction of lipids is preferably effected at elevated temperatures, e.g. 40° to 90° C., although sufficient lipid extraction may be effected in some cases using lower temperatures e.g. 25° to 40° C. The use of the elevated temperatures is preferred as in general, when using such elevated temperatures, the flocculated cells tend to sink in the lipid extraction solvent thus rendering separation of the flocculated cells and lipid extraction solvent facile by techniques such as decanting.

The cells are then contacted with the PHB-extraction solvent. Preferred extraction solvents include 1,2-dichloroethane, methylene chloride and chloroform. Where no preliminary lipid extraction step is employed, the PHB extraction is preferably effected at temperatures below 40° C., whereas higher temperatures, e.g. 50° to 90° C. may advantageously be employed if a preliminary lipid extraction step is utilised.

The lipid extraction step (if used) and/or the PHB extraction may be effected continuously with the flocculated cells packed into a suitable bed.

In one preferred form of the invention the flocculated cells are dried, for example in a fluid bed drier, after lipid extraction. This results in a relatively porous granular material which can then be contacted with the PHB extraction solvent. We have found that with such granular materials, the PHB may readily be leached therefrom leaving the cell debris in the granular form; this granular cell debris can be separated from the PHB-containing solution easily by techniques such as filtration. The porous granular material formed by drying the lipid extracted flocculated cells is particularly suitable for trickle extraction techniques wherein the PHB-solvent is allowed to permeate down through a bed of the granular material.

In another form of the invention the flocculated cells are subjected to a lipid extraction step as described hereinbefore, separated from the lipid extraction solvent and then reslurried in water. The resultant slurry may then be subjected to a 'wet' extraction process, e.g. as described in aforesaid European Patent Application 15123, by adding a liquid that is immiscible with water and in which PHB is soluble to the slurry.

Generally no further cell breakage step, e.g. milling as was proposed for use in some cases in aforesaid European Application 15123, is necessary where the flocculated cells have been subjected to a lipid extraction step.

After agitation of the aqueous slurry with the PHB extraction solvent, the two liquid phases may be separated: the cell debris remains in the aqueous phase while the PHB is dissolved in the solvent phase. The PHB extraction solvents mentioned hereinbefore, viz. chloroform, 1,2-dichloroethane, and methylene chloride may be used to effect the PHB extraction by this process.

Because of the lipid removal step prior to the 'wet' extraction, the formation of emulsions between the two liquid phases is avoided, and separation thereof is relatively simple.

The PHB may be recovered from the solution in the extraction solvent by precipitation into a non-solvent, e.g. a methanol/water mixture or by evaporation of the solvent, e.g. by spray or flash drying.

The invention is illustrated by the following examples:

EXAMPLE 1

An aqueous suspension of *Alcaligens eutrophus* of 150 g $l^{-1}$ biomass content, of which about 45% by weight was PHB, was flocculated by addition of alkali to increase the pH to 9, heated to 90° C. for 10 min and then acidified to pH 5. The resultant flocs were separated from the aqueous medium by decanting.

100 ml of the wet flocs were added to 200 ml of methanol and refluxed for 5 min. The methanol was then removed by decanting and the resultant flocs dried in a fluid bed dried at 60° C. for 20 min. A granular product was formed.

10 g of the granular product were refluxed with 200 ml of chloroform for 5 min to extract PHB. The cell debris was granular and floated on top of the chloroform solution and was readily skimmed therefrom.

The PHB was precipitated from the chloroform solution by adding the solution to a mixture of methanol and water (4 vol. methanol: 1 vol. water). The precipitated PHB was recovered by filtration and dried in an oven at 40° C. The amount of PHB recovered corresponded to about 80% by weight of that in the *Alcaligenes eutrophus* bacterial cells.

The weight average molecular weight of the recovered PHB was 270,000 as measured by gel permeation chromatography.

EXAMPLE 2 (COMPARATIVE)

By way of comparison, PHB was extracted by refluxing 10 g of dried cells (obtained by spray drying the aqueous suspension) with 200 ml of chloroform. The cell debris was in the form of fine particles that could only be separated from the chloroform solution with difficulty.

EXAMPLE 3

Example 1 was repeated except that instead of refluxing the granules with the chloroform, the granules were mixed at room temperature with the chloroform in a Silverson mixer. The cell debris was easier to separate from the chloroform solution than in Example 2 but more difficult than in Example 1.

The amount of PHB recovered was about 50% by weight of that in the bacterial cells.

EXAMPLE 4

It has been proposed in U.S. Pat. No. 3,036,959 to treat wet bacterial cells with acetone prior to extraction with a PHB extraction solvent. The amount of acetone suggested is 1 to 10 times the weight of the cells.

To examine the effect of acetone, to portions of an aqueous suspension containing about 5% by weight of cells of which about 50% by weight was PHB, there were added various amounts of acetone and the mixture shaken for 2 minutes at room temperature.

| Sample | Acetone ml | Cell suspension ml | Result |
|---|---|---|---|
| A | 10 | 90 | No visible effect |
| B | 50 | 50 | The cells assumed a partially flocculated appearance but no separation of the cells from the liquid phase occurred. |
| C | 90 | 10 | The cells assumed a partially flocculated appearance and settled to occupy a volume of about 25 ml. |

Since treatment of wet cells, or the cell suspension, with acetone would give rise to the need to recover the acetone from the acetone/aqueous medium mixture when operated on a large scale, the effect of acetone or dried cells was examined.

Various amounts of spray dried cells, as used in Example 2, or air dried cells, i.e. cells that had been separated from the suspension as used in Example 1 by centrifugation followed by fluid bed drying in air at 40° C., were agitated for 2 minutes with 100 ml of acetone at room temperature, and the suspension left to stand for 1 hour. The cells did not have a flocculated appearance but sedimented to some degree as shown in the following table.

| Sample | Type of cells | Weight of cells (g) | Amount of cells sedimented (g) |
|---|---|---|---|
| D | Spray dried | 2 | trace |
| E | Spray dried | 5 | ~2 |
| F | Spray dried | 10 | ~8 |
| G | Air dried | 2 | trace |
| H | air dried | 5 | ~1 |
| I | air dried | 10 | ~5-6 |

When the sedimented cells of Samples C or F were separated by decanting, dried, and refluxed with chloroform, separation of the cell debris from the chloroform solution was no easier than in Example 2.

We claim:

1. A process for the separation of poly($\beta$-hydroxy butyric acid), PHB, from an aqueous suspension of bacterial cells containing PHB wherein the PHB-containing cells are contacted with an extraction solvent in which PHB is soluble and the solvent having the PHB dissolved therein is separated from the cell debris, characterised in that the bacterial cells in the aqueous suspension are caused to flocculate by the step of reducing the pH of the suspension to a value in the range 2 to 5 by treatment with an acid, in combination with at least one of the steps (i) treatment of the suspension with alkali to increase its pH to a value in the range 8 to 12 before acidification, and (ii) heating the suspension to a temperature within the range 50° to 200° C. before or after acidification, and then the flocculated cells are separated from the aqueous medium prior to contact of the cells with the extraction solvent.

2. A process according to claim 1 characterised in that the cells in the suspension are caused to flocculate by increasing the pH of the suspension to a value in the range 8.5 to 12, heating by injecting steam under pressure into the suspension, and then acidifying the suspension to a pH in the range 3 to 5.

3. A process according to claim 2 characterised in that the cell suspension is heated to a temperature in the range 60° to 100° C. by the injection of steam.

4. A process according to claim 1 characterised in that, prior to contact with the extraction solvent, the lipids associated with the bacterial cells are extracted from the flocculated cells by contact with a solvent in which the lipids are soluble but in which PHB is insoluble, and the solvent having the lipids dissolved therein is separated from the flocculated cells.

5. A process according to claim 4 characterised in that the flocculated cells are contacted with the lipid extraction solvent at a temperature in the range 40° to 90° C.

6. A process according to claim 4 characterised in that the lipid extraction solvent is acetone or methanol.

7. A process according to claim 4 characterised in that, after lipid extraction but before contact with the PHB extraction solvent, the flocculated cells are dried whereby a porous granular product is obtained for contact with the PHB extraction solvent.

8. A process according to claim 1 characterised in that the PHB extraction solvent is selected from chloroform, 1,2-dichloroethane, and methylene chloride.

* * * * *